United States Patent
Berman et al.

[11] Patent Number: 5,885,701
[45] Date of Patent: *Mar. 23, 1999

[54] ODORANT COMPOSITION DELIVERY SYSTEM AND METHOD

[75] Inventors: Michael J. Berman, Southhampton; Michael A. Parrotta, Churchville; Frank Flynn, Scranton, all of Pa.

[73] Assignee: Fragrance Technology Trust, Bellwood, Ill.

[ * ] Notice: The term of this patent shall not extend beyond the expiration date of Pat. No. 5,637,401.

[21] Appl. No.: 831,816

[22] Filed: Apr. 2, 1997

Related U.S. Application Data

[62] Division of Ser. No. 255,280, Jun. 8, 1994, Pat. No. 5,637,401.

[51] Int. Cl.⁶ .................................................. B32B 9/00
[52] U.S. Cl. .................... 428/212; 428/34.3; 428/35.8; 428/35.9; 428/40.1; 428/42.2; 428/43; 428/45; 428/96; 428/192; 428/201; 428/213; 424/59; 424/65; 424/66; 252/315.2; 156/276
[58] Field of Search ................................. 428/201, 40.1, 428/304.4, 42.2, 905, 34.3, 45, 95, 43, 192, 96, 35.9, 35.8, 212, 213; 156/276; 252/315.2, 522 R; 424/59, 65, 66

[56] References Cited

U.S. PATENT DOCUMENTS

| | | | |
|---|---|---|---|
| Re. 33,299 | 8/1990 | Sweeney et al. | 428/201 |
| 2,169,055 | 8/1939 | Overshiner | 167/94 |
| 2,698,824 | 1/1955 | Morgulis | 167/90 |
| 2,907,682 | 10/1959 | Eichel | 117/122 |
| 3,000,486 | 3/1961 | Rua, Jr. et al. | 283/102 |
| 3,159,536 | 12/1964 | Marotta | 167/42 |
| 3,516,846 | 6/1970 | Matson | 117/36.2 |
| 3,570,139 | 3/1971 | Ladd et al. | 35/8 |
| 3,578,482 | 5/1971 | Whitaker et al. | 117/38 |
| 3,655,129 | 4/1972 | Seiner | 239/60 |
| 3,685,734 | 8/1972 | Paciorek et al. | 239/56 |
| 3,897,578 | 7/1975 | Kanda et al. | 427/358 |
| 3,967,880 | 7/1976 | Johnson | 350/133 |
| 3,993,831 | 11/1976 | Vassiliades | 428/307 |
| 4,071,374 | 1/1978 | Minton | 106/189 |
| 4,145,001 | 3/1979 | Weyenberg et al. | 239/56 |
| 4,161,283 | 7/1979 | Hyman | 239/55 |
| 4,243,224 | 1/1981 | Spector | 273/157 |
| 4,254,910 | 3/1981 | Martin | 239/60 |
| 4,285,468 | 8/1981 | Hyman | 239/55 |
| 4,428,869 | 1/1984 | Munteanu et al. | 252/522 |
| 4,487,585 | 12/1984 | Goldwasser | 434/259 |
| 4,487,801 | 12/1984 | Turnbull et al. | 428/313.5 |
| 4,493,869 | 1/1985 | Sweeney et al. | 428/201 |
| 4,528,226 | 7/1985 | Sweeney | 428/40 |
| 4,561,997 | 12/1985 | Roehl | 252/522 |
| 4,564,535 | 1/1986 | Altenschopher et al. | 427/285 |
| 4,582,492 | 4/1986 | Etter et al. | 434/236 |
| 4,605,554 | 8/1986 | Prussin et al. | 424/66 |
| 4,606,956 | 8/1986 | Charbonneau et al. | 428/40 |
| 4,647,433 | 3/1987 | Spector | 422/125 |
| 4,654,256 | 3/1987 | Doree et al. | 428/304.4 |
| 4,687,203 | 8/1987 | Spector | 273/157 |
| 4,710,371 | 12/1987 | Palinczar | 424/47 |
| 4,720,409 | 1/1988 | Spector | 428/46 |
| 4,720,417 | 1/1988 | Sweeney et al. | 428/201 |
| 4,720,423 | 1/1988 | Fraser | 428/313.5 |

(List continued on next page.)

FOREIGN PATENT DOCUMENTS

| 768040 | 9/1997 | Canada | 283/22 |

*Primary Examiner*—William Krynski
*Assistant Examiner*—Abraham Bahta
*Attorney, Agent, or Firm*—Ryndak & Lyerla

[57] ABSTRACT

An odorant composition in the form of a colloidal suspension. A colloidal suspension odorant composition comprised of a colloidal material and a liquid fragrance component is provided. A package comprised of a multiple layer top substrate and a multiple layer bottom substrate is also provided. The colloidal suspension odorant composition may be packaged in the vapor impermeable package and the combination may be used to supply test quantities of odorants.

1 Claim, 2 Drawing Sheets

U.S. PATENT DOCUMENTS

| | | | |
|---|---|---|---|
| 4,726,608 | 2/1988 | Walton | 283/96 |
| 4,738,473 | 4/1988 | Meloni et al. | 283/903 |
| 4,746,567 | 5/1988 | Zelter | 428/321.5 |
| 4,749,569 | 6/1988 | Gianino et al. | 424/65 |
| 4,751,934 | 6/1988 | Moir et al. | 132/79 |
| 4,752,496 | 6/1988 | Fellows et al. | 427/27 |
| 4,769,264 | 9/1988 | Dreger | 428/40 |
| 4,777,035 | 10/1988 | Shin | 424/66 |
| 4,778,153 | 10/1988 | Bachman et al. | 283/101 |
| 4,847,124 | 7/1989 | Lux nee Andrieux | 428/34.2 |
| 4,880,690 | 11/1989 | Szycher et al. | 428/224 |
| 4,889,755 | 12/1989 | Charbonneau | 428/42 |
| 4,925,517 | 5/1990 | Charbonneau et al. | 156/276 |
| 4,925,667 | 5/1990 | Fellows et al. | 424/401 |
| 4,935,401 | 6/1990 | Pendergrass, Jr. | 503/206 |
| 4,936,916 | 6/1990 | Shimmitsu et al. | 106/21 |
| 4,954,285 | 9/1990 | Wierenga et al. | 252/174.11 |
| 4,983,388 | 1/1991 | Kuwata et al. | 424/401 |
| 4,990,381 | 2/1991 | Holzner | 428/35.3 |
| 5,035,886 | 7/1991 | Chakrabarti et al. | 424/78 |
| 5,071,704 | 12/1991 | Fischel-Ghodsian | 428/354 |
| 5,192,386 | 3/1993 | Moir et al. | 156/268 |
| 5,248,537 | 9/1993 | Giannavola | 428/40 |
| 5,306,752 | 4/1994 | Attarwala | 524/167 |
| 5,391,420 | 2/1995 | Bootman et al. | 428/195 |

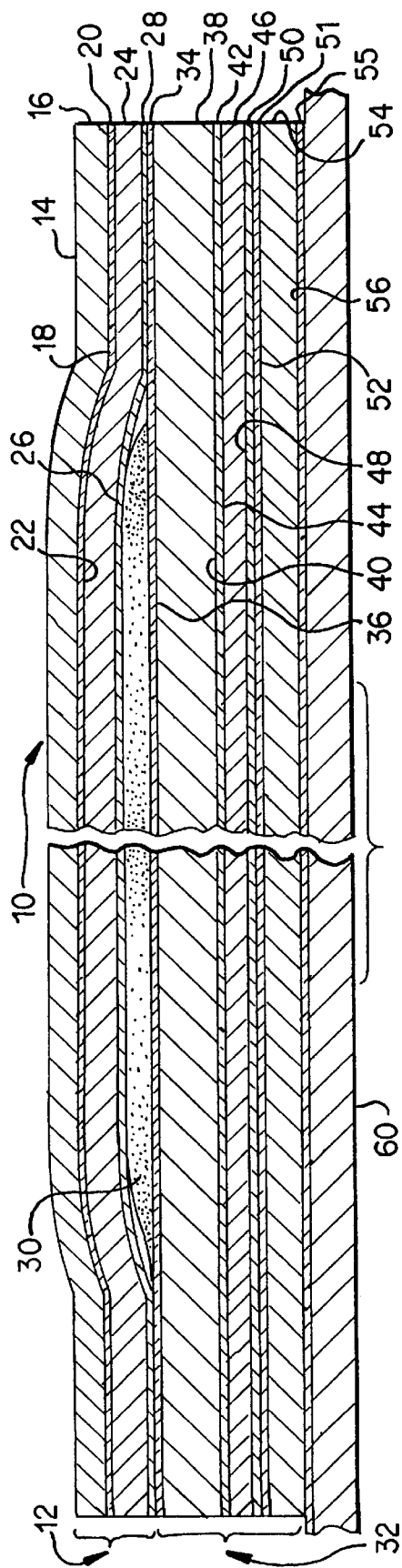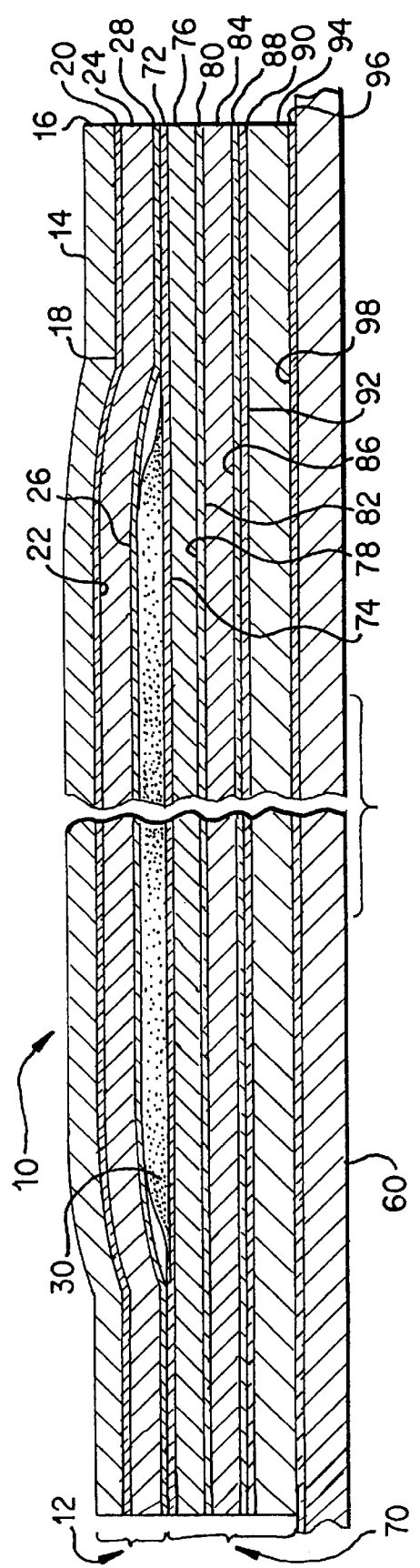

ODORANT COMPOSITION DELIVERY SYSTEM AND METHOD

This is a division of application Ser. No. 08/255,280 filed Jun. 8, 1994, now U.S. Pat. No. 5,637,401.

FIELD OF THE INVENTION

This invention relates generally to an odorant delivery system and method. More particularly, the invention relates to a perfume tester suitable for attachment to a page of a magazine or similar article, for example.

BACKGROUND OF THE INVENTION AND DESCRIPTION OF THE PRIOR ART

A number of devices for containing and otherwise packaging odorants such as perfume fragrances and flavoring agents, natural or synthetic, are known. Perhaps the most commonly known perfume packaging device is a glass bottle, in which a fragrance composition is contained. Typically, a fragrance composition contains a relatively minor amount of the extract of essential oil or oils constituting a perfume fragrance and a relatively major amount of carrier liquid, such as water and/or an alcohol, resulting in a relatively volatile composition of low viscosity. One of the problems with bottled perfume is that if tipped over when open, the contents spill readily, with the spilled liquid perfume likely rendered unusable. Also, because a bottle of perfume generally contains a bulk amount relative to the amount applied by a person in a single application, it is difficult to dispense a precise proper amount for a single application. While trial and error may assist a user in determining the proper amount, a substantial amount of the perfume is likely to be wasted. A need exists for a perfume delivery system and method that dispenses a precise preselected amount of fragrance.

It is often desirable to provide small quantities of odorants or fragrances such as perfume fragrance or flavoring agents to customers or potential customers for various reasons. Small or test quantities of odorant may be used to promote or advertise a fragrance or flavoring, for example. If a person likes the test quantity, purchase of a larger amount of the fragrance or flavoring is more likely. Also, it may be desirable to sell quantities of fragrance packaged in a size intended for a single application. It may also be desirable to send small quantities of perfume or flavoring aromas through the postal system, including as inserts in magazines. While bottles conceivably could be made small enough to contain only a single use amount of perfume, and could be made solid enough to send through the mail, such bottles would not be practical for general use or for inserting into the pages of a magazine.

Some other devices are known for providing odorant testers in magazine advertisements. For example, use of microencapsulated capsules of fragrance adhered to a paper or plastic based substrate are known, as shown in U.S. Pat. No. 4,493,863 to Sweeney. Physical contact or some type of pressure or mechanical action with the microencapsulated capsules is needed to rupture or crush the walls of the microcapsules to allow the fragrance to be released for persons to sense the fragrance. The amount of physical contact required to rupture the capsules is not great and as a result, incidental physical contact often causes the unintended rupture of the microcapsules thereby causing unintended release of the fragrance.

Other known odorant packaging devices include layers of substrates adhered to one another, with the fragrance oils suspended in some medium which is sealed in between the layers of substrates. For example, U.S. Pat. No. 4,880,690 to Szycher describes a system using a polyurethane layer in connection with a fragrance oil to assist in the emission of fragrance.

One problem with existing odorant tester packages is that premature and unintended release of the fragrance occurs. Such premature release occurs during shipment, such as through the mail, resulting in a decreased amount of fragrance available at the time the package is intended to be opened. Because a magazine may contain more than one test quantity of odorant, odorant test packages which allow unintended fragrance release may commingle, thus resulting in a mixture of aromas, rather than a specific, selected aroma. Also, the United States Postal Service has promulgated certain regulations designed to minimize unintended release of fragrance, and may implement additional regulations further restricting banning the mailing of devices that emit fragrance during shipment. Sealed perfume packages of the type taught in U.S. Pat. No. 4,880,690 to Szycher are believed to be susceptible to unwanted fragrance emission. When such perfume packages are placed in a magazine as an insert, a reader is exposed to the fragrance regardless of whether the reader desires such exposure. In the case of persons with certain allergies or sensitivities, such unwanted exposure may present a serious health threat. Vapor permeable fragrance inserts in a magazine may also discourage persons from purchasing the magazine to avoid being exposed to an undesired fragrance. In any event, it is best if people have a choice as to whether to perceive a fragrance.

Solutions containing extracts of essential oil, such as perfume, are well known. Alcohol and/or water is a popular solvent for perfume solutions. With alcohol and/or water as the solvent, the resulting solution, containing mostly solvent, has a very low viscosity. Alcohol is a common solvent because it is highly volatile and evaporates quickly, providing a quick "lift" of the fragrance. "Lift" refers to the speed that a fragrance reaches a person's olfactory senses. When a suspension medium containing alcohol is placed between two substrates of a perfume tester package, certain problems may arise. Specifically, where the two substrates are adhered together by heat, alcohol can chemically interact with the bond formed by heat. For example, the alcohol might attack the heat seal, compromising the integrity of the heat seal and thereby allowing air into the package and fragrance to escape the package. Also, when air is present, alcohol quickens the drying time of the remaining fragrance oils and, without additives, results in a solution of very low viscosity making application by a person from a sample package very difficult. Additionally, alcohol displaces space in the package which otherwise could be used for the odorant.

A need exists for an alcohol-free odorant composition and delivery system that is readily adaptable to use in a perfume tester package for use as a magazine insert or for attachment directly to a magazine page and the like. Such a perfume composition should be easy to apply, handle and remove from such a package.

SUMMARY OF THE INVENTION

In accordance with the present invention, an alcohol-free odorant composition is provided that is especially suitable for use in a perfume tester, such as in a tester package as a magazine insert or attached to a magazine page or the like.

In accordance with the invention, a moist, gel-like odorant composition is provided. The composition has sufficient viscosity such that it does not flow when a test amount is in an odorant tester package and the package is opened. The odorant composition is thus relatively highly viscous yet can be free of viscous, greasy substances such as petrolatum and is not dependent on the presence of such substances to achieve the desired viscosity.

In accordance with another aspect of the present invention, an odorant composition is provided with improved, i.e., longer lasting, odorant retention and emission capabilities when the odorant composition is applied to a surface, such as human skin.

In accordance with another aspect of the present invention, an odorant delivery system is provided that includes a vapor impermeable package or pouch so that no fragrance is emitted from the sealed package. The odorant delivery system remains sealed until opened by a user.

The odorant delivery system of the present invention can contain a preselected amount of a perfume fragrance suitable for a single application.

In accordance with another aspect of the invention, an improved heat sealed pouch is provided for containing an odorant composition. The package and odorant delivery system of the present invention can have a shelf-life of about two years or more.

In addition, the odorant delivery system of the present invention can deliver multiple different fragrances in the same package without commingling any of the other fragrances contained within the package.

The odorant delivery system of this invention can be affixed to any suitable substrate, including coated or un-coated papers, folding cartons, film, etc. using conventional affixing equipment. The odorant delivery system is printable so that a desired message may be imprinted on the visually perceptible portion of the odorant delivery system.

In accordance with the present invention, an odorant composition is provided that is a mixture of a liquid fragrance component (and optionally a diluent) and a solid colloidal material. The odorant generally is present in an amount such that the mixture formed by the combination is a colloidal suspension. Preferably, the solid colloidal material is fumed silica and the resulting composition generally exhibits Newtonian flow properties and is not thixotropic. The fumed silica may be coated with a hydrophobic compound, such as dimethylsiloxane. Preferably, compositions in accordance with the invention have a viscosity between about 200 and 1500 centipoise at 23° C. Generally, the odorant composition is a viscous, gel-like cohesive substance as contrasted with a free flowing powder. By gel-like, it is meant a relatively stiff, viscous composition, i.e., a viscosity between about 200 and 1500 centipoises at 23° C., and not a free flowing powder.

Other solid colloids that may be used in accordance with the invention as the solid colloidal material of the odorant composition include polymeric materials such as acrylic resins like polyacrylate or polymethylmethacrylate or inorganic molecular sieve materials like colloidal clays such as zeolite, bentonite, attapulgite and activated alumina, for example. It is contemplated that other solid colloids may be used in the perfume composition of the present invention as long as the fragrance of the perfume oil is not adversely affected to an unacceptable degree and as long as no other unwanted adverse effects are produced.

The perfume composition may include optional components such as microencapsulated material selected from the group of perfume oil, volatile silicone and mixtures thereof. The microencapsulated material generally may be present in an amount of up to about 10% by weight of the total composition.

To increase "lift" when the package is first opened, unencapsulated volatile liquid silicone can be added to the odorant composition, usually in an amount of up to 20% and preferably about 10% by weight of the odorant composition. The volatile silicone is used to increase lift in place of alcohol. Preferably, volatile silicone having a viscosity of about one centistoke at 23° C. is utilized since this material has an adequate vapor pressure for providing lift.

In accordance with another aspect of the present invention, a heat sealed vapor impermeable package that contains a quantity of a material therein, such as the perfume composition of the present invention is provided. The heat sealed vapor impermeable package comprises a top and a bottom substrate that is heat sealed preferably around the periphery of the package with the odorant composition or other desired material contained therein. The heat seal and the substrates are vapor impermeable, thus forming an effective container for volatile materials such as a perfume composition, for example.

In accordance with one aspect of the present invention, the top substrate of the sealed vapor impermeable package comprises the following layers in order from top to bottom, an outer layer which may be a metallized polymer layer wherein the polymeric portion of the layer may be selected from the group of nylon polypropylene and polyester, and the metallizing agent may be selected from the group of aluminum, copper and iron; an inner aluminum foil layer adhesively secured to the outer layer by a first adhesive layer wherein the first adhesive layer may be a layer of a pressure sensitive adhesive material or an extruded polymeric layer wherein the polymer is selected from the group of polyethylene and polypropylene; and a heat sealable adhesive coating on the aluminum foil opposite the side of the aluminum foil adhesively secured to the outer polyester layer.

The bottom substrate may comprise the following layers in order from top to bottom: a heat sealable adhesive coating; a first layer which may be a metallized polymeric layer wherein the polymeric portion of the layer may be selected from the group of nylon, polypropylene and polyester, and the metallizing agent may be selected from the group of aluminum, copper and iron; a silicon dioxide layer adhesively attached to the first polyester layer; and a second polyester layer adhesively secured to the silicon dioxide layer.

In accordance with another aspect of the present invention, an odorant delivery system is provided that includes a plurality of sealed vapor impermeable packages containing a colloidal suspension odorant composition comprising a colloidal fumed silica and a liquid fragrance component, with the plurality of packages affixed to a carrier web.

In accordance with the present invention, a method of fabricating a vapor impermeable package for containing a material between top and bottom substrates is provided where the top substrate comprises layers, in order from top to bottom, of polyester, adhesive, foil and heat activated adhesive and the bottom substrate comprises layers, in order from top to bottom of a heat sealable adhesive coating, a first polyester layer, an adhesive layer, a silicon dioxide layer, an adhesive layer and a second polyester layer, the steps including: depositing a preselected amount of desired material which may be, for example, an alcohol-free odorant composition onto the inner surface of the bottom substrate; placing the top substrate substantially over the material deposited on the bottom substrate and in substantial registry with the bottom substrate so that the two substrates come into physical contact with one another; and sealing the two substrates together to form a vapor impermeable peripheral heat seal surrounding the desired material.

Also in accordance with the present invention, a method of applying perfume to a desired surface, such as a person's body, is provided. This method includes the steps of opening a sealed package wherein the sealed package comprises a top substrate and a bottom substrate with an amount of a perfume composition between the two substrates, an amount of a perfume composition comprising fumed silica and a liquid fragrance component. The method includes the steps of at least partially breaking the seal between the top substrate and the bottom substrate and peeling one substrate back to expose the perfume composition and thereafter rubbing the perfume composition on the exposed substrate surface to a desired area of perfume application.

BRIEF DESCRIPTION OF THE DRAWINGS

FIG. 3 is a cross-sectional view of the odorant delivery system taken along the line 3—3 of FIG. 1 illustrating the top and bottom substrates including their respective layers and the carrier liner of the odorant delivery system;

FIG. 5 is a cross-sectional view of an alternate embodiment of the odorant delivery system of the invention taken along line 3—3 of FIG. 1 illustrating the layers of the top and bottom substrates including their respective layers and the carrier liner.

DETAILED DESCRIPTION OF THE INVENTION

The Odorant Composition

Figure 1:
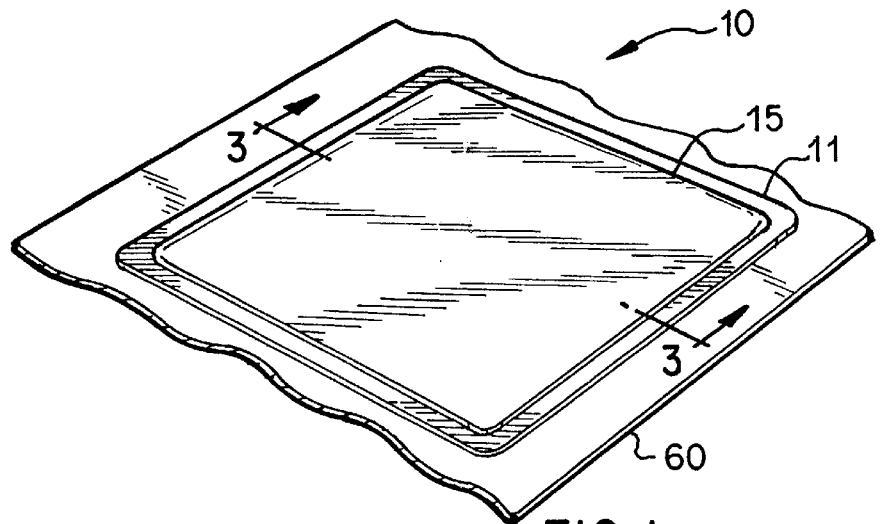
FIG. 1 is a perspective view of the unopened odorant delivery system of the invention that is adhered to the carrier liner.

In accordance with the present invention, a solid-liquid colloidal suspension odorant composition is provided in which the colloidal solid is preferably colloidal fumed silica and the liquid fragrance component may include without limitation, active fragrance ingredients such as essential oil or oils, perfume fragrances or flavoring agents, all of which may be natural or synthetic and a diluent for the active fragrance component, if desired. Such ingredients are preferably present in the odorant composition in amounts such that the suspension exhibits gel-like characteristics. In accordance with a preferred embodiment, the odorant composition is packaged in a vapor impermeable package.

In some instances, it is desirable to dilute the active fragrance ingredient(s) with a suitable diluent such as diethyl phthalate or isopropylmyristate, for example, which is used to lower fragrance concentration without effecting the amount of fumed silica, thereby lessening intensity and conserving fragrance ingredients. The diluent generally may be present in an amount of up to about 70% by weight of the active fragrance ingredient(s).

The colloidal solid and liquid fragrance component typically present in the odorant composition are in a ratio of from about 3 parts colloidal solid to 97 parts liquid fragrance component and about 13 parts colloidal solid to 86 parts liquid fragrance component by weight and preferably a ratio of from about 3 parts colloidal solid to 97 parts fragrance component:14 parts colloidal solid:86 parts fragrance component by weight. The colloidal dispersion can be made by adding a desired amount of colloidal solid to a desired amount of liquid fragrance component. To aid in efficiently mixing the combination, the colloidal solid is preferably added slowly to the liquid fragrance component. The colloidal solid and liquid fragrance component are thoroughly mixed together. The preferred proportions of fumed silica and liquid fragrance component depends on the initial viscosity of the liquid fragrance component and the particle size of the colloidal solid. A preferred viscosity for the colloidal suspension is between 200–1500 centipoises and more preferably between 300–700 centipoises at 23° C. For reference, typical honey at room temperature has a viscosity of about 2000 centipoises. The specific amount of fumed silica added is chosen to alter the viscosity of the liquid fragrance component so that the viscosity of the colloidal suspension falls within this range. In this range of viscosity, small amounts (such as about 0.025 to 0.045 grams) of the colloidal suspension take on a bead-like shape. The colloidal suspension exhibits Newtonian flow properties in that at 23° C., no increase in the suspension's temperature is necessary to make the suspension flowable. The colloidal suspension is not thixotropic. The relatively high viscosity of the odorant composition of the invention makes it easier to handle in the packaging process compared to the relatively low viscosity of just the liquid fragrance component. The colloidal silica also gives the liquid fragrance component more body and renders it easier to apply by the consumer.

The colloidal substance chosen is preferably odorless and has the ability to absorb the liquid fragrance component without affecting fragrance fidelity. A colloidal substance is a solid particulate material in which one or more of the particulate's dimensions generally have a size of from about 1 nanometer to 1 micron. Fumed silica has been found to work well to meet these requirements. The colloidal material is preferably made up of particles which have a particle size of from about 0.05 microns to 1.0 microns, most preferably from about 0.2 microns to 1.0 microns. The colloidal material preferably has a surface area of from about 80 $m^2/g$ to 120 $m^2/g$. The colloidal material should generally be selected such that a substantial or undesired negative interaction with the liquid fragrance component, such as by affecting the fidelity of the fragrance, is avoided. If a particular colloidal material produces an unwanted deleterious effect on the liquid fragrance component, a different colloidal substance should be chosen using the above identified criteria. The preferred fumed silica is treated with an organic compound which may be dimethylsiloxane and its reaction products with the silica. The dimethylsiloxane and fumed silica forms a polymer, polydimethylsiloxane. The organic compound coats the fumed silica and causes it to become hydrophobic, i.e., to reject water. The organic compound also increases the fumed silica's affinity for absorbing oils, including essential oils, perfume fragrance oils and flavoring agent oils. A preferred type of commercially available treated fumed silica is known as hydrophobic silicon dioxide, synthetic silica or colloidal silica or by the brand name CAB-O-SIL® TS-720 treated fumed silica, made by Cabot Corporation, CABOSIL Division, RR#2, Route 36 West, Tuscola, Ill. 61953.

Colloids that can be used in place of silica include polymeric materials such as acrylic resins like polyacrylate and polymethylmethacrylate, commercially available as POLYTRAP® from Dow Corning Corporation, South Saginaw Road, Midland, Mich. 48686 or inorganic molecular sieve materials like colloidal clays such as zeolite, bentonite and activated alumina, for example.

The liquid fragrance component may be obtained from any source including manufacturers of perfume who desire to use the present invention as a means to deliver their perfume fragrance to users or prospective users. The liquid fragrance component of perfume used in the present invention comprises the oil in perfume necessary to provide the perfume fragrance preferably without the additives commonly found in off-the-shelf perfumes (except perhaps in minute, contaminant-level amounts) and generally without a solvent or carrier. For example, off-the-shelf perfumes typically contain a substantial amount of alcohol as the solvent for the essential oils. Alcohol is preferably not used in the odorant composition of the invention.

Additional materials may be added to the odorant composition of the present invention as desired, such as microencapsulated capsules containing volatile silicone, fragrance oils, or other materials as desired or combinations thereof. These microcapsules generally have a size between about 1 micron to 25 microns, and preferably have a size between about 2 microns and 5 microns. These microencapsulated capsules are of a type well known in the art, and may be in a urea/formaldehyde wall, plasticized wall, or preferably, a gelatin wall format, to allow easy crushability.

Microcapsules may be filled with volatile silicone, such as octamethyltrisiloxane, commercially available as Dow Corning 200(R) fluid, made by Dow Corning Corporation, South Saginaw Road, Midland, Mich. 48686. Volatile silicone will increase the lift of the fragrance once the colloidal suspension containing the microencapsulated volatile silicone capsules are applied to a surface such as human skin, but they have no affect on the colloidal suspension in the package. "Lift" is the ability of the fragrance to lift off the package when opened or the surface to which the composition is applied and thus refers to the speed with which the fragrance reaches a person's olfactory senses.

Microcapsules containing a liquid fragrance component, such as essential oil, in the odorant composition of the invention will increase lift life of the odorant composition by placing a portion of the liquid fragrance component in an "on-demand" format. Once the colloidal suspension containing microcapsules of the liquid fragrance component is applied to a surface, such as human skin, the lift can be renewed later on demand by rubbing the colloidal suspension, thereby crushing the microcapsules of liquid fragrance component and thus releasing fragrance for olfactory perception by persons near the surface.

Additionally, as stated earlier, unencapsulated volatile liquid silicone may be added to the composition in an amount of up to about 20% by weight of the odorant composition, preferably in an amount of about 10% by weight of the odorant composition.

The microcapsules containing volatile silicone or liquid fragrance component or other suitable material may be added to the colloidal suspension separately or in combination. These capsules or other material may be added to the colloidal suspension at any time in the mixing process. Care must be taken to ensure that the colloidal suspension is well mixed to ensure the thorough distribution of the microcapsules or other material. The addition of microcapsules or other material necessarily will displace certain proportionate amounts of fumed silica and liquid fragrance component from the colloidal suspension. Generally up to about 10% by weight of the colloidal suspension may contain microcapsules containing volatile silicone or liquid fragrance component, other matter and mixtures thereof (i.e., either microencapsulated mixtures of materials and/or mixtures of microcapsules containing different material).

In addition to being especially suitable for packaging in an envelope, the odorant compositions of the invention have other advantages. When applied to the skin, it is believed that the odorant composition in accordance with the invention lasts longer than conventional perfumes. While not wishing to be bound by theory, it is believed that the improved retention and emission is due at least in part to the use of a solid colloid and in particular, use of fumed silica as the colloidal solid. Colloids such as fumed silica have a very large surface area and have micropores contained within each colloidal particle. When mixed with a colloid such as fumed silica, sorption of the liquid fragrance component onto the fumed silica occurs and, as a result, the large surface area of the colloidal material has the fragrance thereon. Additionally, the active ingredient of the odorant composition, the liquid fragrance component, is preferably comprised of oil, in the form of essential oil or oils, perfume fragrance oils or flavoring agent oils. Most perfumes are contained in a solution of water and/or alcohol, both of which dissipate relatively quickly. By using oil instead of the more volatile water and/or alcohol, the odorant composition lasts longer and retains fragrance longer than conventional odorant delivery systems.

The Vapor Impermeable Package

The colloidal suspension odorant composition described above is preferably contained in a package. The preferred package is a vapor impermeable multiple layer package comprising a top substrate and a bottom substrate. The package may be affixed to a carrier liner for ease in subsequent handling. The combination of the top substrate, colloidal suspension and the bottom substrate, when sealed, creates a vapor impermeable package, thus ensuring that no fragrance escapes prematurely, that is, before the intended use by the consumer. Also, when sealed, the package is unlikely to open accidentally, further ensuring that fragrance does not escape unintentionally.

Figure 2:
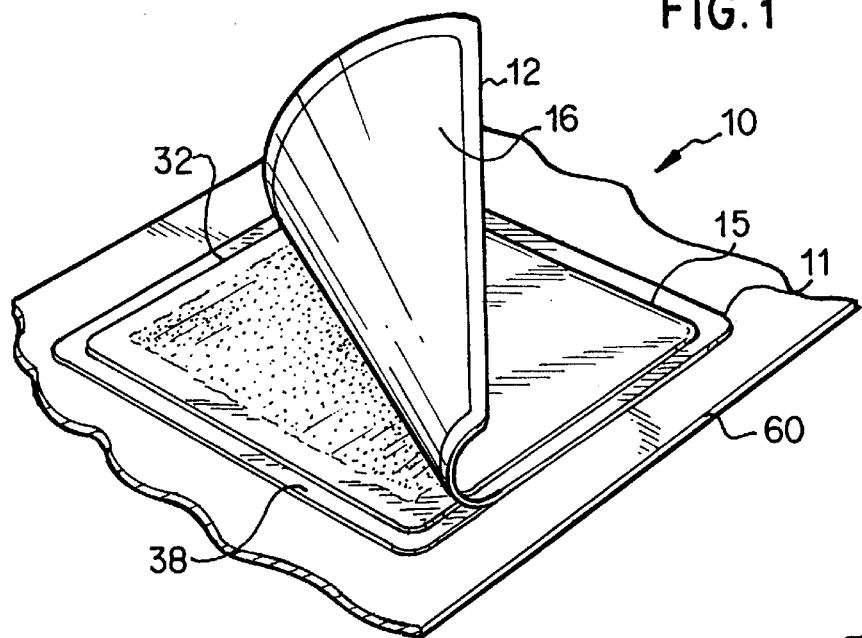
FIG. 2 is a perspective view of the odorant delivery system attached to the carrier liner, which is partially opened exposing the odorant composition of the present invention.

Turning now to the drawings, FIG. 1 shows a perspective view of an odorant delivery system 10 composed of an unopened vapor impermeable package composed of a top substrate 12 and a bottom substrate 32 adhered to a carrier liner 60. Package 11 contains odorant composition 30 therein between substrates 12 and 32 which are peripherally heat sealed together by a heat seal 15. As shown in FIG. 2, top substrate 12 of package 10 may be opened up by peeling top substrate 12 from bottom substrate 32. Opening package 11 requires breaking at least a portion of heat seal 15 between top substrate 12 and bottom substrate 32. Opening package 11 exposes moist, gel-like colloidal suspension 30 and allows fragrance to lift off package 11 and be perceived by nearby persons' olfactory senses. Colloidal suspension odorant composition 30 may be easily rubbed onto a surface such as human skin directly or indirectly such as with a person's finger.

FIG. 3 is a cross-sectional view of odorant delivery system 10 taken along Line 3—3 of FIG. 1. FIG. 3 shows in cross-section the various portions of the system 10, including layers 16, 20, 24 and 28 of top substrate 12 and layers 34, 38, 42, 46, 50, 51, 54 and 55 of bottom substrate 32, colloidal suspension odorant composition 30, and carrier sheet 60. Top substrate 12 comprises several layers, including polyester layer 16, adhesive layer 20, foil layer 24 and heat activated film coating layer 28. Outermost layer 16 preferably comprises polyester such as MYLAR® made by Dupont de Nemours, E. I. & Co., Wilmington, Del. 19898. Alternative embodiments of layer 16 may include layer 16 comprising a metallized film layer made up of polypropylene, nylon or polyester metallized on one surface with an agent consisting of a metal selected from the group consisting of aluminum, copper or iron. Outer surface 14 of polyester layer 16 may be treated or top coated (not shown) with a vinyl resin such as Union Carbide VYNS to enhance printability. Outermost layer 16 may be between about 0.5 mils and 1.5 mils thick, preferably about 1 mil thick. A layer of adhesive 20 such as a pressure sensitive adhesive is placed on inner surface 18 of the outermost layer 16. Adhesive 20 may be treated with a pigment such as titanium dioxide to render it opaque and to create a desired color, such as white. Adhesive layer 20 alternatively may comprise an extruded polymer such as polyethylene or polypropylene extruded between webs of adjacent outer layer 16 and foil layer 24. The adjacent layers may be pressed together to effect a bond therebetween. Adhered to inner surface 18 of outermost layer 16 by adhesive 20 is a layer of foil 24, which may aluminum foil, preferably dead-soft aluminum foil. Foil layer 24 may be from about 0.00025 gauge to about 0.00040 gauge, preferably about 0.00035 gauge. Attached to inner surface 26 of foil 24 is a film coating 28, preferably a thermoplastic or heat activated film coating, such as SURLYN® made by Dupont de Nemours, E.I. & Co., Wilmington, Del. 19898. Film coating 28 may be adhesively secured to foil layer 24 by a layer of adhesive such as a pressure sensitive adhesive (not shown) or film coating 28 may be extruded onto foil layer 24 to bond thereto. Film coating 28 generally is from about 0.75 mils to about 1.0 mils thick, preferably about 0.75 mils thick.

Bottom substrate 32 comprises several layers, including heat activated film coating layer 34, polyester layer 38, adhesive layer 42, silicon dioxide layer 46, adhesive layer 50, adhesive layer 51, polyester layer 54 and adhesive layer 55.

The outermost layer 54 of bottom substrate 32 is a preferably a layer of polyester which may have layers of adhesive 51 and 55 adhered to it on each surface 52 and 56. Preferably, polyester layer 54 and its surrounding adhesive layers 51 and 55 may be in the form of a polyester double sided tape containing an acrylic pressure sensitive adhesive on each side of the tape. An example of the acrylic adhesive used in connection with the double sided tape is that made by Rohm & Haas No. 1085, Rohm & Haas, Independence Mall West, Philadelphia, Pa. 19105. This tape may be from about 0.5 mils to 1.5 mils thick, preferably about 0.5 mils thick. Adhesive layer 51 alternatively may comprise an extruded polymer such as polyethylene or polypropylene to bond silicon dioxide layer 46 to polyester layer 54. Adhesive layer 55 may be a pressure sensitive adhesive or may comprise an extruded polymer such as polyester or polypropylene to bond polyester layer 54 to carrier liner 60.

Outermost layer 54 is only needed when the package is intended to be affixed to carrier liner 60. Adhered to the inner surface 52 of the outermost layer 54 is a layer 46 of silicon dioxide such as POLYGLAS® made by Dow Corning Corporation, South Saginaw Road, Midland, Mich. 48686. Silicon dioxide layer 46 may be from about 0.5 mils to 1.0 mils thick, preferably about 0.75 mils thick. A layer of adhesive 50 is placed on outer surface 48 of silicon dioxide layer 46 to assist in adhering silicon dioxide layer 46 to outermost layer 54. Adhesive layer 50 may be a pressure sensitive adhesive or may comprise an extruded polymer such as polyester or polypropylene to bond silicon dioxide layer 46 to polyester layer 54.

Adhered to outer surface 48 of silicon dioxide layer 46 is a layer of polyester 38 such as MYLAR® made by Dupont de Nemours, E.I. & Co., Wilmington, Del. 19898, which contains a low co-weight acrylic pressure sensitive adhesive 42 on its outer surface 40. Alternative embodiments of layer 38 may include layer 38 comprising a metallized film layer made up of polypropylene, nylon or polyester metallized on one surface with an agent consisting of a metal selected from the group consisting of aluminum, copper or iron. Polyester layer 38 may be between about 1.5 and 2.5 mils thick, preferably about 2 mils thick.

Adhered to inner surface 36 of polyester layer 38 is a layer 34 of film coating, preferably a heat activated film coating such as SURLYN® made by Dupont de Nemours, E.I. & Co., Wilmington, Del. 19898. Film coating 34 may be adhesively secured to polyester layer 38 by a layer of adhesive such as a pressure sensitive adhesive (not shown) or film coating 34 may be extruded onto polyester layer 38 to bond thereto. Film coating 34 may be from about 0.75 mils to about 1.0 mils thick, preferably about 0.75 mils thick.

Turning now to FIG. 5, which shows in cross-section an alternative embodiment of the various portions of package 10, including the layers of top substrate 12 and bottom substrate 70, colloidal suspension 30, and carrier sheet 60. Top substrate 12 comprises the same layers discussed above, but bottom substrate 70 is different. Bottom substrate 70 comprises several layers including heat activated film coating 72, foil layer 76, adhesive layer 80, silicon dioxide layer 84, adhesive layer 88, adhesive layer 90, polyester layer 94 and adhesive layer 96. In this alternative embodiment, outermost layer 94 of bottom substrate 70 is a preferably a layer of polyester which may have adhesive layers 90 and 96 adhered to it on each surface 92 and 98, preferably by use of a polyester double sided tape containing an acrylic pressure sensitive adhesive on each side of the tape. An example of the acrylic adhesive used in connection with the double sided tape is that made by Rohm & Haas No. 1085, Rohm & Haas, Independence Mall West, Philadelphia, Pa. 19105. This tape may be from about 0.5 mils to 1.5 mils thick, preferably about 0.5 mils thick.

Adhered to inner surface 92 of outermost layer 94 is a layer 84 of silicon dioxide such as POLYGLAS® made by Dow Corning Corporation, South Saginaw Road, Midland, Mich. 48686. Silicon dioxide layer 84 may be from about 0.75 mils to 1.25 mils thick, preferably about 1 mil thick. An adhesive layer 88 is placed on outer surface 86 of silicon dioxide layer 84 to assist in adhering silicon dioxide layer 84 to outermost layer 94. Inner surface 82 of silicon dioxide layer 84 is adhered to a layer of foil 76, such as aluminum foil, preferably dead-soft aluminum foil. Foil layer 76 may be from about 0.00025 gauge to about 0.00040 gauge, preferably about 0.00035 gauge.

Outer surface 78 of foil layer 76 is adhered to inner surface 82 of silicon dioxide layer 84 by adhesive layer 80. Attached to inner surface 74 of foil layer 76 is a film coating 72, preferably a heat activated film coating, such as SURLYN® made by Dupont de Nemours, E.I. & Co., Wilmington, Del. 19898. Film coating 72 may be from about 0.75 mils to about 1.0 mils thick, preferably about 0.75 mils thick.

In another preferred embodiment, one or more additional layers may be placed in the bottom substrate. One additional layer preferably comprises polyethylene, preferably in a range of about 1.0 to 2.0 mils thick, most preferably about 1 mil thick. The preferable location for this additional layer is between the middle layer and the inner layer.

With any of the embodiments, a carrier liner 60 may be used in the production and affixing processes. The carrier liner is preferably not used until after top substrate 12 is adhered to bottom substrate 32 or 70. After top substrate 12 is adhered to bottom substrate 32 or 70, preferably through a heat sealing process, then the combined unit or package is adhered to carrier liner 60 through adhesive layer 55 or 96 on outer surface 56 or 98 of double sided tape 54 or 94 on bottom substrate 32 or 70. Carrier liner 60 is preferably polypropylene and may be from about 1.5 mils to about 2.5 mils thick, preferably about 2.0 mils thick. Carrier liner 60 is preferably somewhat transparent or translucent, allowing the ability to see into the back of the package for quality control purposes. A preferred embodiment of the carrier liner may be made of 40# to 60# semi-bleach Kraft (preferably 40#) or most preferably 2 mil polypropylene which makes the contents visible.

Figure 4:
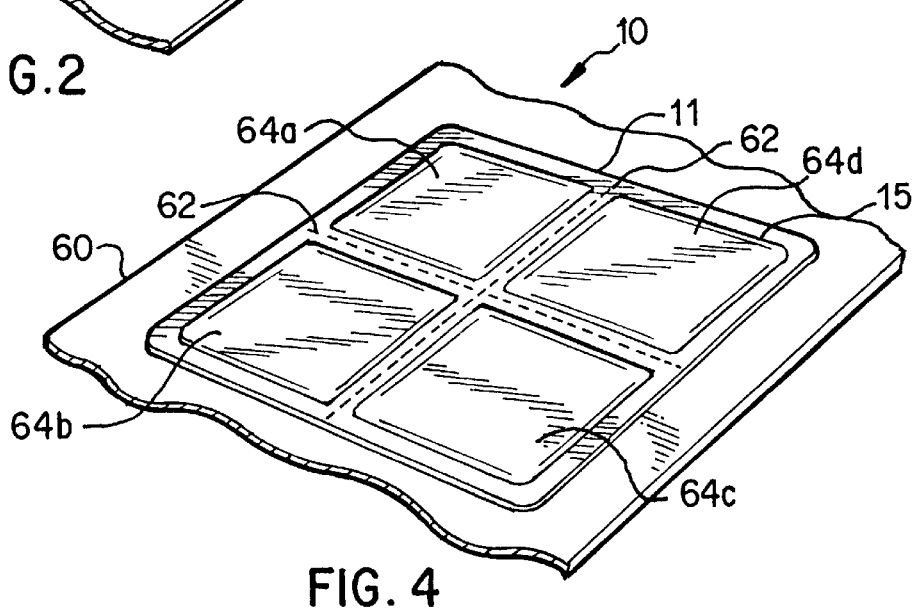
FIG. 4 is a perspective view of an alternate embodiment of the invention wherein the odorant delivery system has multiple portions allowing multiple fragrances to be contained within a single odorant delivery system with no fragrance intermixing.

As shown in FIG. 4, package 10 may contain perforations 62 in top substrate 12 and bottom substrate 32 (not shown). The perforations 70 in top substrate 12 and bottom substrate 32 (not shown) correspond with one another. Perforations 62 facilitate easy separation of individual portions 64a–d of package 11 along perforations 62. The separated individual package portions such as portion 64a of package 11 may be opened separately from the remaining portions 64b–d of package 11, as shown in FIG. 2 for a non-perforated package 11. Any pattern of perforations may be used to create any shape of package portions 64a–d.

The Assembly Process

Assembly of the vapor impermeable odorant delivery system is performed on presses typically used in the publishing, printing or label industry, such as flexographic, letter press or web offset press units. Label presses such as those made by Mark Andy or Webtron may be used. The presses should be equipped with triple unwind units so that three separate and distinct layers can be handled separately through the equipment. One unwind unit is used for top substrate 12, the second unwind unit is used for bottom substrate 32 or 70 and the third unwind unit is used for carrier liner 60. Outermost surface 14 of top substrate 12 is the only surface on which ink is actually printed. The bottom substrate receives the deposit of the colloidal suspension or other product a user desires to seal in this package. The carrier liner is used to provide a base on which to affix the package.

Standard flexo, letter press or webbed print stations are used for printing the outer surface 16 of the outermost layer 14 of the top substrate 12. The top substrate 12 passes through the print and UV stations, whereas the bottom substrate 20 bypasses these stations. The print and UV stations print the packages 10, and finish the outer surface 14 of the packages 10.

Bottom substrate 32 passes through a metered applicator or spitter. The metered applicator may use multiple individual solenoids and standard drive train equipment, capable of measuring the amount of product required to be deposited on the bottom substrate, with the viscosity ranges established, preferably within 5% of the desired fill weight. Multiple solenoids may be utilized so that multiple fragrances may be deposited in the same package. The number of solenoids used may be varied depending on the number of desired fragrances to include in the same package. In addition to the metered applicator, a closed pump system using disposable inserts may be used. Disposable inserts may be used so that none of the essential oils dissipate or contaminate the plant or the manufacturing process. In a preferred embodiment, the pump system is capable of holding a minimum of one ounce of material and a maximum of 55 gallons of material per pump with up to 4 pumps connected to 4 solenoids and nozzle heads. Alternatively, in place of the metered applicator or spitter, flexographic deposition, screen print or gravure print application methods may be used. Top substrate 12 bypasses the metered applicator and the closed pump system.

The colloidal suspension is deposited onto heat activated film coating layer 34 or 72 of bottom substrate 32 or 70 as a bead of viscous substance, then is immediately covered by heat seal adhesive layer 28 of top substrate 12. Top substrate 12 and bottom substrate 32 or 70 unit passes through the heat seal dies upside down, with the bottom substrate the primary seal source to the top substrate. The heat seal dies perform several functions. They press the top substrate and the bottom substrate together. Because the bead of viscous substance or colloidal suspension is immediately between the two substrates, as they are pressed together, the bead of viscous substance flattens out. As the substrates are pressed closer together, a substantial portion of the air is expelled from the area between the two substrates. The heat seal die also, of course, applies heat to the substrates, with contact on either substrate or both substrates simultaneously, for example, causing the thermoplastic coatings to fuse to one another where they are pressed into direct physical contact with one another. The integrity of the heat seal is a function of dwell time and temperature. Dwell time is the amount of time the substrates are in physical contact with the heat seal die. A shorter dwell time is preferable, as more packages 10 can be processed in a shorter period of time with a shorter dwell time. The dwell time is variable, directly related and proportionate to the temperature of the heat seal die. The shorter the dwell time, the higher the temperature must be. Too high of a temperature can result in package 10 which is difficult to open, or may negatively affect the integrity of the fragrance and the colloidal suspension 30. In a preferred embodiment, two heat seal dies or a combination of radiant heat and one heat seal die are used in series, each successively applying heat to the package 10 in the area of intended seal. By using two heat seal dies in series or a combination of radiant heat and one heat seal die in series, the temperature may be reduced in the heat seal die unit(s). By using two heat seal dies in series, or a combination of radiant heat and one heat seal die, dwell time is reduced overall. By reducing the dwell time, press speeds can be dramatically increased. As an alternative, dual heat seal dies can be placed so that both substrates pass between opposed heat seal dies.

The package is die-cut and the matrix removed. The matrix is the left-over area of the package outside the die-cut area. Before removal of the matrix, the package 10 is adhered onto the carrier liner 60. The carrier liner 60 bearing the packages may be wound into a roll of finished product. A roll is easy to use in subsequent processing steps, for example, for automated insertion of the packages onto a preprinted magazine page or other preprinted page, for example. The roll is then placed on a re-wind machine for quality control inspection through use of an optical scanner or a visual inspection. This quality control step allows the replacement of any defective packages.

The finished product including the package 10 filled with a preselected amount of colloidal suspension 30 or other product must be able to withstand pressures at least up to 500 pounds per square inch (psi), the generally accepted standard in the magazine industry, without bursting. If too much colloidal suspension 30 is deposited on the bottom substrate 32 or 70 for sealing within the package, the sealed package 10 may be more susceptible to bursting when subjected to pressure. The preferred amount of colloidal suspension 30 to deposit on the bottom substrate 32 is completely dependant on the size and shape of the package 10 and varies from case to case. As an example, in a package which measures 1¾" by 1¾" square with a fill area of about 1 5/16"×1 5/16" square, an amount of colloidal suspension 30 between about 0.025 and 0.09 grams may be used, preferably an amount between 0.025 grams and 0.045 grams may be used and most preferably an amount between about 0.03 and 0.045 grams (0.04 grams is the most preferred) to achieve a fill amount of about 0.023 grams per square inch of fill area. Any distortions in amount are preferably greater than 0.03 grams as opposed to less than 0.03 grams, up to preferably no more than 0.045 grams. Amounts of colloidal suspension less than 0.03 grams tend to provide too little colloidal suspension to provide an adequate amount of fragrance to the user.

Thus, it is apparent that there has been provided, in accordance with the invention, an odorant delivery system that fully satisfies the objects, aims and advantages set forth above. While the invention has been described in conjunction with specific embodiments thereof, it is evident that many alternatives, modifications, and variations will be apparent to those skilled in the art in light of the foregoing descriptions. Accordingly, it is intended to embrace all such alternatives, modifications and variations as fall within the spirit and broad scope of the appended claims.

What is claimed is:

1. An odorant delivery system comprising a plurality of sealed vapor impermeable packages containing an odorant composition which is a colloidal suspension comprising a colloidal fumed silica and a liquid fragrance component, said plurality of packages affixed to a carrier web.

* * * * *